US00PP22027P2

(12) United States Plant Patent
Michalik

(10) Patent No.: US PP22,027 P2
(45) Date of Patent: Jul. 12, 2011

(54) GERANIUM PLANT NAMED 'FIWOBIC'

(50) Latin Name: *Pelargonium×hortorum*
Varietal Denomination: Fiwobic

(75) Inventor: Andrea Michalik, Dresden (DE)

(73) Assignee: Elsner PAC Jungpflanzen, Dresden (DE)

( * ) Notice: Subject to any disclaimer, the term of this patent is extended or adjusted under 35 U.S.C. 154(b) by 0 days.

(21) Appl. No.: 12/655,601

(22) Filed: Dec. 31, 2009

(51) Int. Cl.
*A01H 5/00* (2006.01)

(52) U.S. Cl. ..... Plt./325

(58) Field of Classification Search ..... Plt./325
See application file for complete search history.

*Primary Examiner* — Susan B McCormick Ewoldt
(74) *Attorney, Agent, or Firm* — C. A. Whealy

(57) ABSTRACT

A new and distinct cultivar of Zonal *Geranium* plant named 'Fiwobic', characterized by its upright and rounded plant habit; freely branching habit; vigorous growth habit; star-shaped dark green-colored leaves; freely flowering habit; star-shaped red purple and white bi-colored flowers; and good garden performance.

1 Drawing Sheet

Botanical designation: *Pelargonium×hortorum*.
Cultivar denomination: 'FIWOBIC'.

BACKGROUND OF THE INVENTION

The present invention relates to a new and distinct cultivar of Zonal *Geranium* plant, botanically known as *Pelargonium×hortorum*, and hereinafter referred to by the name 'Fiwobic'.

The new Zonal *Geranium* plant is a product of a planned breeding program conducted by the Inventor in Dresden, Germany. The objective of the breeding program is to create new uniform Zonal *Geranium* plants with star-shaped flowers and attractive foliage and flower coloration.

The new Zonal *Geranium* plant originated from a cross-pollination made by the Inventor in Dresden, Germany during the summer of 2004 of two unnamed proprietary selections of *Pelargonium×hortorum*, not patented. The new Zonal *Geranium* plant was discovered and selected by the Inventor as a flowering plant from within the progeny of the stated cross-pollination in a controlled environment in Dresden, Germany in June, 2005.

Asexual reproduction of the new Zonal *Geranium* plant by vegetative terminal cuttings in a controlled environment in Dresden, Germany since January, 2006, has shown that the unique features of this new Zonal *Geranium* plant are stable and reproduced true to type in successive generations.

SUMMARY OF THE INVENTION

The cultivar Fiwobic has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fiwobic'. These characteristics in combination distinguish 'Fiwobic' as a new and distinct cultivar of Zonal *Geranium:*

1. Upright and rounded plant habit.
2. Freely branching habit.
3. Vigorous growth habit.

4. Star-shaped dark green-colored leaves.
5. Freely flowering habit.
6. Star-shaped red purple and white bi-colored flowers.
7. Good garden performance.

Plants of the new Zonal *Geranium* differ primarily from plants of the parent selections in plant vigor and flower color.

Plants of the new Zonal *Geranium* can be compared to plants of the *Pelargonium×hortorum* 'Fiwocher', disclosed in U.S. Plant Pat. No. 13,026. In side-by-side comparisons conducted in Dresden, Germany, plants of the new Zonal *Geranium* differed from plants of 'Fiwocher' in the following characteristics:

1. Plants of the new Zonal *Geranium* were shorter than plants of 'Fiwocher'.
2. Flowers of plants of the new Zonal *Geranium* had broader petals than flowers of plants of 'Fiwocher'.
3. Plants of the new Zonal *Geranium* and 'Fiwocher' differed in flower color.

Plants of the new Zonal *Geranium* can also be compared to plants of the *Pelargonium×hortorum* 'Fiworewhi', disclosed in U.S. Plant Pat. No. 14,188. In side-by-side comparisons conducted in Dresden, Germany, plants of the new Zonal *Geranium* differed from plants of 'Fiworewhi' in the following characteristics:

1. Plants of the new Zonal *Geranium* were shorter than plants of 'Fiworewhi'.
2. Flowers of plants of the new Zonal *Geranium* had broader petals than flowers of plants of 'Fiworewhi'.
3. Plants of the new Zonal *Geranium* and 'Fiworewhi' differed in flower color.

BRIEF DESCRIPTION OF THE PHOTOGRAPH

The accompanying colored photograph illustrates the overall appearance of the new Zonal *Geranium* plant, showing the colors as true as it is reasonably possible to obtain in colored reproductions of this type. Colors in the photograph may differ slightly from the color values cited in the detailed botanical description which accurately describe the colors of the new Zonal *Geranium* plant. The photograph comprises a side perspective view of a typical flowering plant of 'Fiwobic' grown in a container.

DETAILED BOTANICAL DESCRIPTION

The aforementioned photograph and following observations, measurements and values describe plants grown in 19-cm containers in Dresden, Germany in a glass-covered greenhouse during the summer and under conditions which closely approximate commercial Zonal *Geranium* production. During the production of the plants, day temperatures averaged 18° C., night temperatures averaged 16° C. and light levels ranged from 15 kilolux to 100 kilolux. Plants were four months old when the photograph was taken, and plants were nine months old when the description was taken. In the detailed description, color references are made to The Royal Horticultural Society Colour Chart, 1995 Edition, except where general terms of ordinary dictionary significance are used.

Botanical classification: *Pelargonium×hortorum* 'Fiwobic'.

Parentage:

*Female, or seed, parent.*—Unnamed proprietary selection of *Pelargonium×hortorum*, not patented.

*Male or pollen parent.*—Unnamed proprietary selection of *Pelargonium×hortorum*, not patented.

Propagation:

*Type.*—By vegetative terminal cuttings.

*Time to initiate roots, summer.*—About 18 days at temperatures of 20° C.

*Time to initiate roots, winter.*—About 22 days at temperatures of 20° C.

*Time to produce a rooted young plant, summer and winter.*—About four weeks at temperatures of 20° C.

*Root description.*—Fine, fibrous; white in color.

*Rooting habit.*—Freely branching; dense.

Plant description:

*Plant/growth habit.*—Upright to rounded plant habit; densely foliated; vigorous growth habit; freely basal branching habit with about 22 lateral branches developing per plant.

*Plant height, to top of umbels.*—About 30 cm.

*Plant height, to top of leaves.*—About 22 cm.

*Plant width.*—About 50 cm.

*Lateral branches.*—Length: About 15 cm. Diameter: About 8 mm. Internode length: About 1.5 cm. Texture: Slightly pubescent. Color: Close to 144A.

Foliage description:

*Arrangement.*—Alternate and opposite; simple.

*Length.*—About 4 cm.

*Width.*—About 7 cm.

*Shape.*—Star-shaped.

*Apex.*—Pointed.

*Base.*—Cordate to hastate.

*Margin.*—Lobed.

*Venation pattern.*—Palmate.

*Texture, upper and lower surfaces.*—Smooth, glabrous.

*Color.*—Developing and fully expanded leaves, upper surface: Close to 137A; venation, close to 137A. Developing and fully expanded leaves, lower surface: Close to 147B; venation, close to 146C. Zonation pattern: Faint. Location of zone: Towards margin. Width: About 2 cm. Color: Close to 147A. Petiole: Length: About 4 cm. Diameter: About 2 mm. Texture, upper and lower surfaces: Waxy. Color, upper and lower surfaces: Close to 146B.

Flower description:

*Flower arrangement.*—Single star-shaped flowers arranged in rounded hemispherical umbels arising from apical leaf axils; umbels displayed above the foliar plane on strong peduncles; flowers; flowers face upright to outward depending on the position in the umbel.

*Fragrance.*—None detected.

*Quantity of flowers.*—Freely flowering habit; about 40 umbels develop per plant; each umbel with about 40 flower buds and open flowers.

*Flowering season.*—Year-round under greenhouse conditions; in the garden in Dresden, Germany, flowering is continuous from April until frost in the autumn.

*Flower longevity.*—Individual flowers last about six to ten days on the plant; umbels last about three to four weeks on the plant; flowers not persistent.

*Umbel height.*—About 6 cm.

*Umbel diameter.*—About 9 cm.

*Flower diameter.*—About 4 cm.

*Flower depth (height).*—About 1.5 cm.

*Flower buds.*—Length: About 7 mm. Diameter: About 4 mm. Shape: Roughly elliptic. Color: Close to 144A.

*Petals.*—Quantity per flower: Five in a single whorl; petals non-imbricate. Length, upper petals: About 2 cm to 2.2 cm. Width, upper petals: About 7 mm. Length, lower petals: About 1.7 cm to 2.2 cm. Width, lower petals: About 1.2 cm to 1.5 cm. Shape: Roughly oblong. Apex: Pointed or emarginate. Base: Attenuate. Margin: Serrated. Texture, upper and lower surfaces: Smooth, glabrous. Color: When opening, upper surface: Close to 52A with random streaks, close to 155D. When opening, lower surface: Close to 58B with random streaks, close to 52D. Fully opened, upper surface: Close to 58B with random streaks, close to 155D; ground color becoming closer to 58C with development; venation, close to 58B. Fully opened, lower surface: Close to 58B with random streaks, close to 52D; venation, close to 73B.

*Sepals.*—Quantity per flower: Five, arranged in a single whorl. Length: About 7 mm. Width: About 3 mm. Shape: Lanceolate. Apex: Acute. Margin: Entire. Texture, upper and lower surfaces: Pubescent. Color, upper and lower surfaces: Close to 166A.

*Peduncle (umbel stem).*—Length: About 13 cm. Diameter: About 4 mm. Strength: Strong. Angle: Mostly erect or outwardly slanted. Texture: Pubescent. Color: Close to 144A.

*Pedicel (individual flower stem).*—Length: About 3 cm. Diameter: About 2 mm. Strength: Strong; flexible. Texture: Pubescent. Color: Close to 166A.

*Reproductive organs.*—Androecium: Stamen quantity per flower: About eight. Anther length: About 2 mm. Anther shape: Tubular. Anther color: Close to 52A. Pollen amount: Scarce. Pollen color: Close to 167A. Gynoecium: Pistil quantity per flower: One. Pistil length: About 8 mm. Stigma shape: Five-parted. Stigma color: Close to 58A. Style length: About 4 mm. Style color: Close to 58A. Ovary color: Close to 138D.

*Seed/fruit.*—Seed and fruit development have not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind and temperatures ranging from about 1° C. to about 35° C. and have demonstrated good garden performance.

It is claimed:

1. A new and distinct Zonal *Geranium* plant named 'Fiwobic' as illustrated and described.

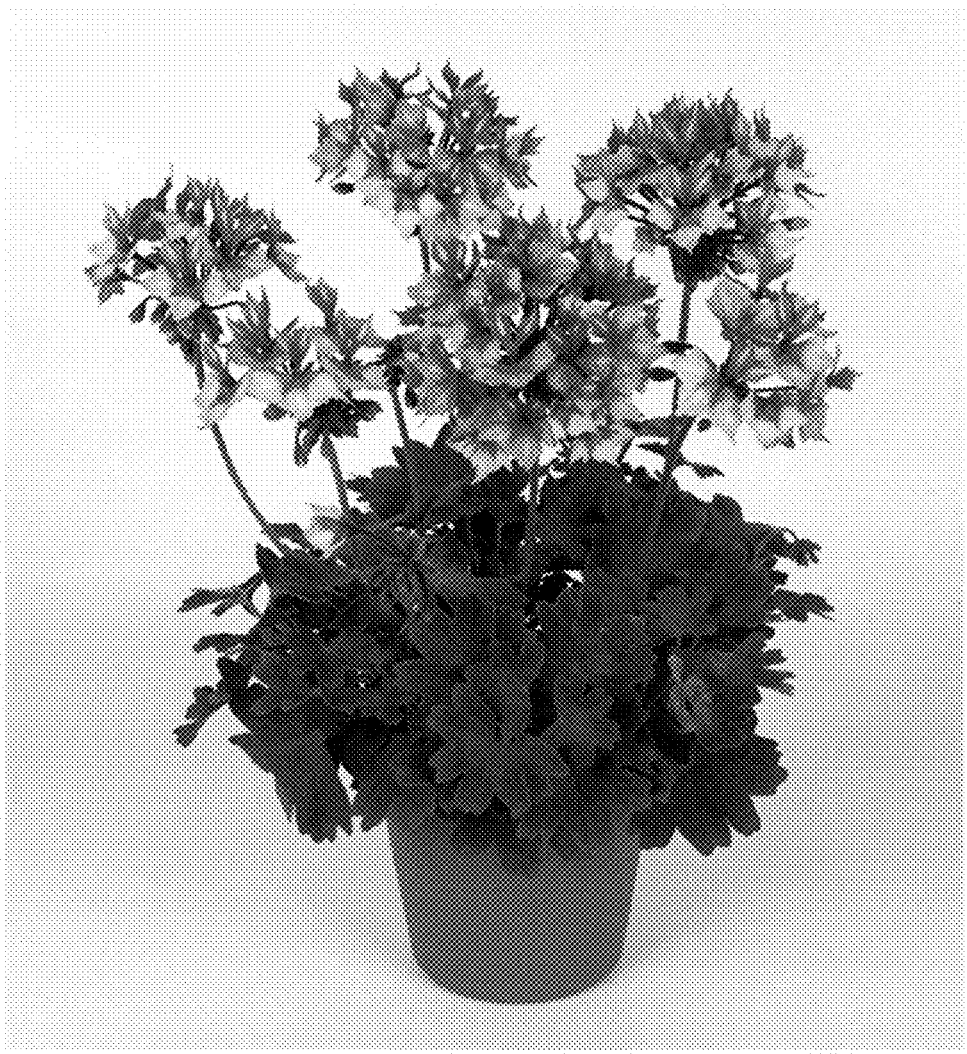

* * * * *